United States Patent [19]
Pettit et al.

[11] Patent Number: 4,816,444
[45] Date of Patent: Mar. 28, 1989

[54] CELL GROWTH INHIBITORY SUBSTANCE

[75] Inventors: George R. Pettit, Paradise Valley; Cherry L. Herald; Yoshiaki Kamano, both of Tempe, all of Ariz.

[73] Assignee: Arizona Board of Regents, Arizona State University, Tempe, Ariz.

[21] Appl. No.: 71,924

[22] Filed: Jul. 10, 1987

[51] Int. Cl.$^4$ .................. C07G 7/00; A61K 37/02
[52] U.S. Cl. ............................ 514/17; 530/330; 548/204
[58] Field of Search ............. 548/204; 514/17, 19; 530/330

[56] References Cited

U.S. PATENT DOCUMENTS 4,414,205  1/1983  Pettit .................................. 514/21
4,486,414  12/1984  Pettit ................................. 514/21

Primary Examiner—Robert Gerstl
Attorney, Agent, or Firm—Richard R. Mybeck

[57] ABSTRACT

A potent cell growth inhibitory substance obtained from the Indian Ocean sea hare Dolabella, herein denominated "dolastatin 10"; and pharmaceutical preparations containing same; and methods useful for the treatment of a host afflicted with neoplastic disease therewith.

18 Claims, No Drawings

CELL GROWTH INHIBITORY SUBSTANCE

INTRODUCTION

The present invention relates generally to cell growth inhibition and more particularly to a potent cell growth inhibitory substance herein denominated "Dolastatin 10" which is obtained from the Indian Ocean sea hare Dolabella, to pharmaceutical preparations containing Dolastatin 10 as their essential active ingredient, and to methods of using such preparations to treat an afflicted host therewith.

Financial assistance was provided by the National Cancer Institute PHS Grant CA-16049-08-11 and numerous private foundations.

BACKGROUND OF THE INVENTION

The great Roman natural scientist Gaius Plinius Secundus (Pliny and Elder) in his comprehensive study, circa 60 AD, first described a most potent Indian Ocean sea hare of the genus Dolabella. (The Romans first designated Mollusca of the family Aplysidae as sea hares because of the similarity between the ears of a hare and the auriculate tentacles of these gastropods). However a consideration of the potential of the Indian Ocean Dolabella with respect to modern medical problems is only of recent origin. (See Pettit's U.S. Pat. Nos. 4,414,205, Nov. 8, 1983, Dolastatins 1–3; and 4,486,414, Dec. 4, 1984, Dolastatins A and B).

The dolastatins may correspond to the potent *D. auricularia* consituents (See: 1969 Ph. D. dissertation of M. Watson. U. of Hawaii, "Some Aspects of the Pharmacology, Chemistry and Biology of the Midgut Gland Toxins of Some Hawaiian Sea Hares, especially *Dolabella auricularia* and *Aplysia pulmonica*", University Microfilms, Inc., Ann Arbor, MI.)

The biological properties exhibited by the sea hare *Dolabella auricularia* have been pursued for centuries but it was only in 1972 that this laboratory found Indian Ocean specimens of this captivating sea hare which yielded extracts that proved effective (over 100% increase in life span) against the U.S. National Cancer Institute's (NCI) murine P388 lymphocytic leukemia (PS system). Subsequently, this laboratory succeeded in isolating nine new (and powerful) cell growth inhibitory and/or antineoplastic peptides which we designated dolastatins 1–9.

Of the early work, dolastatin 1 was found to be the most active (lowest dose) antineoplastic substance (33% cure rate against the NCI murine B16 melanoma at 11 µg/kg) known in its time. Because of the dolastatin's potency, the sea hare seems to require only vanishingly small quantities (about 1 mg each fromm 100 kg), making isolation and structural elucidation of these peptides exceptionally challenging. The present disclosure is based on the isolation and structural determination of a unique linear pentapeptide herein denominated "dolastatin 10". This new substance may well be the most important *Dolabella auricularia* antineoplastic constituent located to date. Indeed, dolastatin 10 appears to be the most active (lowest dose) antineoplastic substance presently known, having shown a 17–67% curative response at 3.25–26 µg/kg against the NCI human melanoma xenograph (nude mouse), 42–138% life extension at 1.44–11.1 µg/kg using the B16 melanoma and 69–102% life extension at 1–4 µg/kg against the PS leukemia ($ED_{50}=4.6\times10^{-5}$ µg/ml).

BRIEF SUMMARY OF THE INVENTION

The present invention relates to the discovery of a new and highly potent cell growth inhibitory substance denominated "Dolastatin 10" which is extracted from the Indian Ocean sea hare Dolabella in the manner hereinafter described in detail. The substance, its synthetic counterpart and non-toxic pharmaceutically acceptable derivatives can be formulated into useful pharmaceutical preparations having demonstratable and confirmable levels of anticancer activity when measured by the generally accepted protocols in use at the United States National Cancer Institute.

Accordingly a principal object of the present invention is to provide a new agent useful in the retardation or remission of one or more types of cancer.

Another object of the present invention is to provide methods and procedures for isolating an antineoplastic substance from marine life in a form in which it may be readily and usefully employed in the therapeutic treatment and management of one or more types of cancer which occur in human hosts.

A further object of the present invention is to provide means and methods of creating useful pharmaceutical preparations for the treatment and management of neoplastic disease which preparations contain as their essential active ingredient a factor obtained from the Indian Ocean sea hare Dolabella, its synthetic counterpart, or a non-toxic pharmaceutically active derivative thereof.

These are still further objects as shall hereinafter appear are readily fulfilled by the present invention in a remarkably unexpected manner as will be readily discerned from the following detailed description of an exemplary embodiment thereof.

DETAILED DESCRIPTION OF THE INVENTION

The Organism

Taxonomy:

Dolabella species belong to the family Aplysidae, the class Gastropoda and the phylum Mollusca. In a reference by H. Engel in "Zoologische Mededeelingen," Leiden, 24, 197–239 (1945), there are numerous color plates of specimens of Dolabella. Also in this reference is a listing of previously presumed different species of Dolabella which were later found to be the same and identified a *Dolabella auricularia*. These species are: Dolabella agassizi, D. andersonii, D. hasseltii, D. hemprichii, D. neira, D. peronii, D. rumphii, D. teremidi, D. tongana, D. truncata, D. variegata, and D. scapula.

In appearance, the Dolabella used were olive green in color with a pear-shaped body and average length, 15–20 cm. The reference by H. Engel has detailed descriptions of Dolabella collected around the world.

The Dolabella collection site used for initial isolation of the dolastatins was on the eastern side of Mauritius in the Indian Ocean, approximate location, 21 S latitude, 56 E longitude, in 4–5 ft. deep water off the coast of the island.

Another site where Dolabella can be collected is near Negros Island in the Philippines, approximate location 9 N latitude, 123 E longitude. Extracts of Dolabella species from five separate collections all contained antineoplastic activity.

Isolation and Purification of Dolastatin

A variety of methods can be used to isolate and purify the various dolastatins from samples of sea hare, such as, solvent extraction, partition chromatography, silica gel chromatography, liquid-liquid distribution in a Craig or Ito apparatus, adsorption on resins, and crystallization from solvents.

Isolation of Dolastatin 10

A combined ethanol-2-propanol extract of D. auricularia (1,000 kg wet, collected in 1982) was concentrated to an active methylene chloride fraction by a series of solvent partition steps. Extensive column chromatographic separation (steric exclusion and partition on Sephadex, partition and adsorption on silica gel and HPLC) using gradient elution techniques guided by PS bioassay led to 28.7 mg of pure dolastatin 10 as a colorless amorphous powder (from methylene chloride-methanol): $C_{42}H_{68}N_6O_2S$ by HREIMS (M+ obs. av. 784.4899; calcd for 784.4921); mp. 107–112 C° (amorphous solid); $[\alpha]_D^{29} -68°$ (C=0.01, methanol; Rf 0.43 in 90:10:0.8:0.2 $CH_2Cl_2$—$CH_3OH$—$H_2O$—$NH_4OH$; and UV$\lambda_{max}$($CH_3OH$), 216 ($\epsilon$ 20,180), and 242 ($\epsilon$ 3,609)nm.

Vigorous hydrolysis of dolastatin 10 under acidic (6N HCl; 110°; 24 h and 70 h) or basic (aq. $Ba(OH)_2$, 120°, 20 h) conditions followed by amino acid analysis of the products consistently gave evidence of valine and phenylalanine. The latter observation was not in complete accord with initial NMR spectral data and was a source of concern until a structure for the new masked Phe named dolaphenine was deduced. Meanwhile, dolastatin 10 was found refactory to simple acetylation and saponification reactions suggesting a cyclic peptide, but eliminating a depsipeptide structure.

Compelling evidence for a linear pentapeptide structure was obtained by partial hydrolysis (in addition to above acidic and basic conditions, hydrolysis with 1:1 conc. HCl and propionic acid for 15 min at 160° C. was performed) followed by conversion of the products to N-trifluoroacetyl butyl esters corresponding to units Dov-Val, Dil, Dap and Deo minus $C_2H_8O$ from loss of the two methoxy groups (from Dil and Dap) and addition of water (to Dap). By means of detailed gas chromatographic separation followed by HREI mass spectrometry (ZAB-2F, Kratos MS-80 and MS-50 instruments), the C-terminal unit Doe was found to lack a butyl ester and the N-terminal segment (Dov-Val), a trifluoroacetyl group. At this point extensive high resolution mass and $^1H$- and $^{13}C$-NMR (400 MHz using $^1H$-$^1H$-COSY, (see: Bax, et al, J. Magn. Reson, 1981, 44,542) 2D-J resolved (see: Aue et al, J. Chem. Phys., 1976, 64,4226) and $^1H$-$^{13}C$-2D shift correlation methods (see: Bodenhausen et al, J. Magn. Reson. 1977, 28,471 and Bax et al, J. Magn. Reson, 1980, 40,213)) spectral studies (see Mass Spectral Fragmentation, below) had already been analyzed and structures ascertained for the four hitherto unknown amino acid constituents leaving only the correct sequence in question.

The dolastatin 10 sequence was unequivocally assigned on the basis of SP-SIMS measurements in conjunction with the unimolecular and collision activated (induced) decomposition (CAD or MS/MS or tandem mass spectrometry) of the SP-SIMS ions (and fragments resulting from decarbonylation, see Table II). The SP-SIMS ion at m/z 227 yields m/z 100 as nearly the only CAD fragment ion indicating good stability for the immonium ion, $(CH_3)_2 N=CH[CH(CH_3)_2]$. Of the two final sequences namely Dov-Val-Dap-Dil-Doe or Dov-Val-Dil-Dap-Doe, the latter was found correct by CAD in conjunction with HREIMS (see Mass Spectral Fragmentation, shown below) experiments using the intact peptide. The final confirmation of the structure for dolastatin 10 was obtained by H-[$^1H$]-NOE difference NMR experiments as summarized in Table I. The amino acid sequence of dolastatin 10 was thereby established. The NOE experiments in $CD_2Cl_2$ combined with 2D-NMR COSY techniques in three solvents ($C_6D_6$, $CD_2Cl_2$ and $CD_3OD$) allowed recognition of Dil as an Ile rather than an Leu derivative. In addition, L-Dov-Ome and racemic Doe HBr were synthesized and the respective H- and $^{13}C$-NMR data was found to nicely approximate chemical shifts assigned to their counterparts in dolastatin 10.

Interestingly, the Dil unit is an O-methyloxy Ile-class relative of the Leu-type amino acid statine (3-hydroxy-4-amino-6-methyl-heptanoic acid) found in the marine tunicate antineoplastic components didemnins A-C (3R,4S) and the lower plant acid protease inhibitor (e.g. of renin and pepsin) pepstatin (3S,4S). A 2-methyl Ala-analog appears in the anticancer antibiotic drug bleomycin (3S,4R). The significance of such amino acid-derived aldol condensation products in anticancer drug design has been greatly increased by the present discovery of dolastatin 10 which corresponds to structural formula:

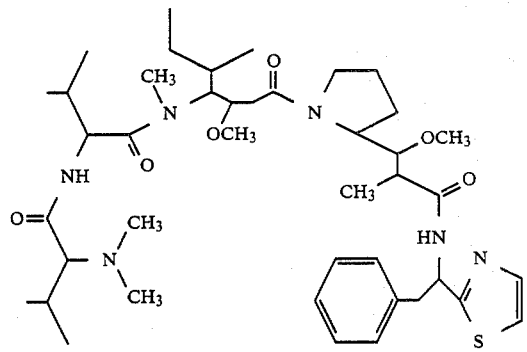

The Tables I and II and the Mass Spectral Fragmentation and Numbering System, referred to above, now appear.

TABLE I

Dolastatin 10 Correlated $^{13}C$— and $^1H$—NMR Assignments in Dichloromethane-$d_2$ Solution

| Structure Assignment | 13C(mult) | Chemical Shift, ppm $^1H$(mult; J, Hz; Integration) | NOE |
| --- | --- | --- | --- |
| 2 | 170.51(s) | 7.717(d; 3.3; 1H) | |
| 4 | 142.77(d) | 7.254(d; 3.3; 1H) | |
| 5 | 118.76(d) | 5.516(ddd; 5.7, 7.2, 9.3; 1H) | |
| 6 | 53.02(d) | 3.399(dd; 5.7, 14; 1H) | |
| 6a | 41.48(t) | 3.256(dd; 5.7; 14; 1H) | |
| 6b1 | 137.74(s) | 7.243(d; 7.9; 2H) | |
| 6b2, 6b6 | 128.74(d) × 2 | 7.214(dd, 7.9, 9.2; 2H) | |
| 6b3, 6b5 | 129.80(d) × 2 | 7.194(t; 9.2; 1H) | |
| 6b4 | 127.02(d) | 7.256(t; 7.6; 1H) | 9, 9a, 10, 10ab, 11 |
| 7 | | | |
| 8 | 175.67(s) | 2.282(quintet; 7.2; 1H) | 7 |
| 9 | 44.79(d) | 1.085(d; 7.1; 3H) | |
| 9a | 14.49(q) | 3.845(dd; 2.0, 8.2; 1H) | 7 |
| 10 | 82.05(d) | 3.309(s; 3H) | 6, 7 |
| 10ab | 60.89(q) | 3.985(m, 1H) | |
| 11 | 59.86(d) | 1.804(ddd; 5.5, 7.0; 19; 1H) | |

TABLE I-continued
Dolastatin 10 Correlated $^{13}$C— and $^1$H—NMR Assignments in Dichloromethane-$d_2$ Solution

| Structure Assignment | $^{13}$C(mult) | Chemical Shift, ppm $^1$H(mult; J, Hz; Integration) | NOE |
|---|---|---|---|
| 12 | 25.00(t) | 1.608(ddd; 7; 9.2, 19; 1H) | |
|    |          | 1.446(ddd; 4.7, 7, 19; 1H) | |
| 13 | 25.45(t) | 1.715(ddd; 4.7, 7.8, 12.7; 1H) | |
|    |          | 3.401(dd; 7.8, 10; 1H) | 17 |
| 14 | 48.03(t) | 3.390(m, 1H)$^b$ | |
| 16 | 174.01(s) | | |
| 17 | 38.11(t) | 2.394(ABq; 9.0; 2H) | 14 |
| 18 | 78.86(d) | 4.122(broad t; 8.7; 1H) | |
| 18ab | 58.16(q) | 3.313(s; 3H) | 22 |
| 19 | 54.11(d) | 3.26–3.39(1H)$^c$ | |
| 19a | 33.62(d) | 1.680(1H)$^b$ | |
| 19b | 26.25(t) | 1.370(broad m, 1H) | |
| | | 1.000(broad m; 1H)$^b$ | |
| 19c | 10.92(q) | 0.823(t; 7.4; 3H) | |
| 19d | 19.82(q) | 1.003(d; 6.8; 3H) | |
| 20a | 30.09(q) | 3.012(s; 3H) | 22 |
| 21 | 171.39(s) | | |
| 22 | 54.20(d) | 4.761(dd; 6.5, 8.8; 1H) | 18, 18ab, 20, 19 |
| 22a | 31.42(d) | 1.983(sextet; 6.7; 1H) | |
| 22b | 18.18(q) | 0.941(d; 6.8; 3H) | |
| 22c | 16.09(q) | 0.977(d; 6.8; 3H) | |
| 23 | | 6.861(d; 8.9; 1H) | 25bc |
| 24 | 172.44(s) | | |
| 25 | 76.77(d) | 2.454(d; 6.9; 1H) | 23 |
| 25bc | 49.92(q) × 2 | 2.262(s; 6H) | 23 |
| 26 | 28.08(d) | 2.073(sextet; 6.7; 1H) | |
| 27 | 20.24(a) | 0.964(d; 6.8; 3H) | |
| 28 | 18.18(q) | 0.902(d; 6.8; 3H) | |

$^a$Residual CHDCl$_2$ as internal reference (5.32 ppm).
$^b$Overlapping signal.
$^c$Signal assigned from NOE data.

TABLE II
Collision-induced Disassociations of Selected Higher Masses from the SP-SIMS[11] Fragmentation of Dolastatin 10

| Parent ions | 785 M + H | 559 $z_2$ + H | 458 $w_3$ | 412 $e_3$ |
|---|---|---|---|---|
| Daughter ions$^{a,b}$ | 753 M + H − CH$_3$OH | 188$^c$ $x_5$ | 426 $w_3$ − CH$_3$OH | 100 $b_1$ |
| | 100 $b_1$ and/or ($z_2/b_3$) | 205 $z_4$ | 86 ($w_3/e_3$) | 214 ($y_2/e_3$) |
| | 188$^c$ $x_5$ | 374 $z_3$ + 2H | 188 $x_5$ | 380 $e_3$ − CH$_3$OH |
| | 559 $z_2$ + 2H | 100 ($z_2/b_3$) | 356 205 | 352 $d_2$ − CH$_3$OH |
| | 154 ($z_2/e_3$ + H) − CH$_3$OH | 154 ($z_2/e_3$ + H) − CH$_3$OH | $z_4$ + 2H 170 | 311 ($y_1/e_3$) − H |
| | 205 $z_4$ + 2H | 170 ($z_3/e_4$) + H | 170 ($z_3/e_4$) + H | 253 |
| | 458 $w_3$ | 138 ($z_3/e_4$) + H − CH$_3$OH | 138 ($z_3/e_4$) + H − CH$_3$OH | 227 $c_2$ |
| | 170 ($z_3/e_4$) + H | 527 $z_2$ + H − CH$_3$OH | 303 $w_4$ | 368 ($x_1/e_3$) |

$^a$See the Mass Spectral Fragmentation below;
$^b$The eight strongest daughter ions are listed in order of decreasing abundances;
$^c$The very abundant m/z 188 ion seems to mask a m/z 186 ($z_2/e_3$ + H), but its daughter ion appears at m/z 154

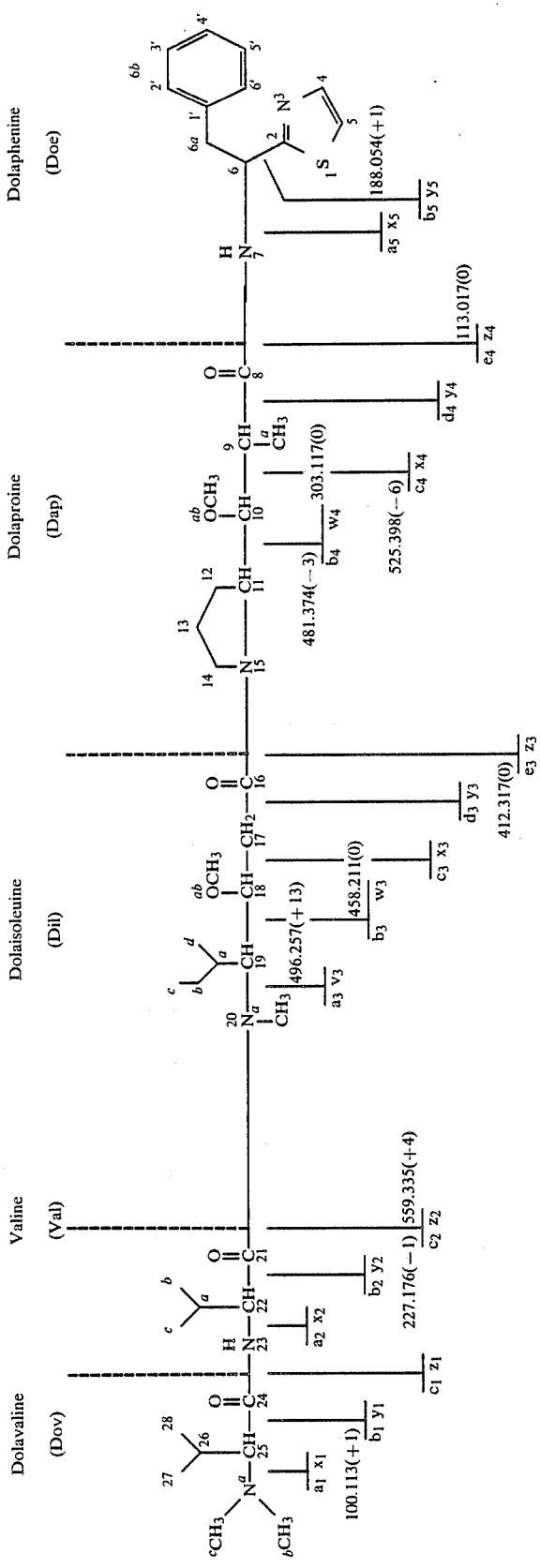

To further assist in the understanding of the present invention, a more detailed discription of the experimental procedures follows.

General Methods

Solvents used for chromatographic procedures were redistilled. The Sephadex LH-20 (25–100μ) employed for gel permeation and partition chromatography was obtained from Pharmacia Fine Chemicals AB, Uppsala, Sweden. Gilson FC-200 race track and FC-80 microfractionators connected to Gilson HM UV-visible Holochrome detectors were used for chromatographic fractionation experiments. Column chromatographic procedures with silica gel utilized the 70-230 mesh or silica gel 60 prepacked columns supplied by E. Merck (Darmstadt). A Partisil M9 10/50 ODS-2 (C-18 reverse phase) column (9.4 mm i.d.×500 mm) was used for HPLC and obtained from Whatman, Inc. Clifton, N.J. Preparative layer plates were also obtained from Whatman, Inc. and the silica gel GF Uniplates for TLC were supplied by Analtech, Inc., Newark, Delaware. The TLC plates were viewed with UV light, developed with an anisaldehyde-acidic acid-sulfuric acid spray (heating at approx. 150° for 10 min) or with ceric sulfate-sulfuric acid (heating for 10 min).

Amino acid analyses were performed with a Beckman Model 121 unit. Ultraviolet spectra were recorded using a Hewlett-Packard 9450A UV/VIS spectrophotometer equipped with a HP7225A plotter. The infrared spectra were recorded with a Nicolet MX-1 FT instrument. High resolution SP-SIMS mass spectra were obtained using. V.G. Analytical MM ZAB-2F and Kratos MS-50 triple analyzer mass spectrometers. High resolution electron impact mass spectra (m/$\Delta$m~10,000) were recorded on Kratos MS-80 and MS-50 instruments, along with CAD spectra. Gas chromatography-mass spectrometry (GC-MS) of suitable derivatives were performed with a J & W fused silica DB-5 (0.243 mm×30 m) column. Successive GC-MS procedures employed chemical ionization (m/$\Delta$m 1,000, reagent NH), low resolution (m/$\Delta$m 1,000) and high resolution (m/$\Delta$m 3,000) electron impact methods. The NMR experiments (in various solvents using a Bruker 5-mm $^1$H$^{13}$C dual switchable probehead) were conducted using a Bruker AM-400 narrow bore spectrometer with an ASPECT 3000 computer and pulse programmer operating at 400.13 and 100.62 MHz for $^1$H-and $^{13}$C-NMR, respectively.

Animal Collection, Extraction, and Preliminary Experiments

The Western Indian Ocean (Mauritius) sea hare Dolabella auricularia was initially collected in October 1972. By March 1975 confirmed activity of an ethanol extract against the National Cancer Institute's (NCI) P388 lymphocytic leukemia (PS system) was established and showed T/C 235 at 600 mg to 167 at 176 mg/kg. A series of analogous extracts from subsequent recollections of the sea hare gave comparable results. The experiments reported herein were conducted with a 1982 recollection (same site) preserved in ethanol. The total volume of animal (~1,000 kg) and ethanol preservative was 700 gallons.

After extraction and solvent partitioning 2.75 kg of methylene chloride concentrate was obtained for large-scale preparative HPLC. Two columns in series (6"×10') were packed with silica gel (Davisil 633, 200–400 mesh, slurry packed in 7:3 hexane-ethyl acetate). The 2.75 kg of dark (green-black) concentrate was dissolved in ethyl acetate (2 gal) and pumped onto the column and chromatographed using the following solvent gradients at a rate of 60–72 l/h.

| Eluent | Eluent Vol. (l) | Fraction No. | Fraction Residue (g) |
|---|---|---|---|
| 70/30 hexane:ethyl acetate | 200 | 1 | 64.9 |
| 60/40 hexane:ethyl acetate | 120 | 2–8 | 282 |
| 50/50 hexane:ethyl acetate | 240 | 8–9 | 78 |
| | | 10–14 | 160.1 |
| | | 15–16 | 58 |
| | | 17–18 | 72.2 |
| 100% ethyl acetate | 120 | 19–21 | 74.9 |
| | | 22–25 | 70.6 |
| 95:5:0.7 ethyl acetate-methanol-water | 120 | 26–28 | 156.4 |
| | | 29–31 | 50.5 |
| 83:17:1.4 ethyl acetate-methanol-water | 240 | 32–35 | 42.7 |
| | | 36–38 | 50.3 |
| | | 39 | 66.2 |
| | | 40 | 76 |
| | | 41–45 (A) | 132 |
| 67:33:2.5 ethyl acetate-methanol-water | 240 | 46–50 (B) | 72 |
| | | 51 | 77 |
| | | 52–55 | 209.5 |
| 50:50:5 ethyl acetate-methanol-water | | 56–60 | 56 |
| 45:45:10 ethyl acetate-methanol-water | | 61–65 | 100 |
| | | 66–69 | 30.5 |

Each fraction was eluted with 20 l of solvent and comparable (by TLC) fractions were combined.

Isolation of Dolastatin 10

From the preparative HPLC fractions, two displayed significant activity in the P388 system, fraction A (132.0 g PS T/C toxic→165 at 30→7.5 mg/kg and ED$_{50}$<10$^{-2}$) and fraction B (72.0 g, PS T/C toxic→141 at 35→8.7 mg/kg and ED$_{50}$<10$^{-2}$). The fractions were combined and dried to give 190.4 g. An aliquot (38 g) was treated as shown below in Series I, Separation Schemes Part 1 and Part 2.

Separation Scheme - Part 1

Fraction A (38 g)
Series I
T/C (mg), toxic - 16.5 (30-7.5)

LH-20 Sephadex
1:1 CH$_2$Cl$_2$—CH$_3$OH

C   D   E   F   G   H   J

-continued
Separation Scheme - Part 1

| | | | | | | | |
|---|---|---|---|---|---|---|---|
| Wt(mg) | 2.4 | 7.9 | 4.1 | 3.9 | 1.7 | 5.9 | 0.6 |
| $ED_{50}$ | 16 | $3.4 \times 10^{-4}$ | $2.3 \times 10^{-3}$ | 1.5 | 0.25 | 1.1 | 2.4 |
| T/C(mg) | | toxic $(29 \rightarrow 3.6)$ | toxic $(22 \rightarrow 2.7)$ | | | | |

(6.0 g) I-1
silica gel
990:10:0.1
100:100:1
EtOAc—$CH_3OH$—$H_2O$ (6.0 g) I-2
silica gel
99:1 → 1:1
$CH_2Cl_2$—$CH_3OH$

| | K | L | M | N |
|---|---|---|---|---|
| Wt(g) | 0.395 | 0.771 | 1.44 | 0.580 |
| $ED_{50}$ | $1.9 \times 10^{-2}$ | $1.9 \times 10^{-2}$ | $1.9 \times 10^{-2}$ | 56 |
| T/C(mg) | toxic → 138 $(13 \rightarrow 3.2)$ | toxic $(11 \rightarrow 2.7)$ | toxic → 140 $(11 \rightarrow 2.7)$ | toxic $(17 \rightarrow 2.1)$ |

Separation Scheme - Part 2

Combined Fractions, K,L,M (2.6 g)
silica gel
99:1 → 1:1
$CH_2Cl_2$—$CH_3OH$

Fraction N (0.58 g)
LH-20 Sephadex
4:5:1
hexane-$CH_2Cl_2$—$CH_3OH$

| | O | P | Q | R | S | T | U |
|---|---|---|---|---|---|---|---|
| Wt(mg) | 78.5 | 76.2 | 211.5 | 191.0 | 594.2 | 101.8 | 88.2 |
| $ED_{50}$ | $8.9 \times 10^{-3}$ | $3.0 \times 10^{-3}$ | $3.6 \times 10^{-4}$ | 49.5 | 25.5 | $1.6 \times 10^{-3}$ | $3.5 \times 10^{-2}$ |
| T/C(mg) | toxic → 102 $(6.6 \rightarrow 0.83)$ | 86 → 120 $(5 \rightarrow 0.63)$ | toxic $(6.6 \rightarrow 0.85)$ | 121 → 98 $(6.5 \rightarrow 0.82)$ | toxic → 156 $(7.8 \rightarrow 0.98)$ | | |

(1.15 g)
(1) silica gel
99:1 → 4:1
$CH_2Cl_2$—$CH_3OH$
(155.8 mg)
(2) silica gel
99:1 → 1:1
EtOAc—$CH_3OH$—$H_2O$ silica gel
99:1 → 1:1

| | V | W | X |
|---|---|---|---|
| Wt(mg) | 1.1 | 6.3 | 18.1 |
| $ED_{50}$ | $<10^{-4}$ | $<10^{-4}$ | $4 \times 10^{-4}$ |

(1) prep TLC
9:1:0.08
$CH_2Cl_2$—$CH_3OH$—$H_2O$
(2) prep TLC
9:1:0.1
EtOAc—$CH_3OH$—$H_2O$
(3) LH-20 Sephadex
5:5:1
hexane-$CH_2Cl_2$—$CH_3OH$ (5.0 mg) Dolastatin 10

HPLC
Partisil-10
ODS-2
1:1 → 9:1
$CH_3OH$—$H_2O$ (3.8 mg)

The major portion (152 g) was separated in a similar Series II as described in Separation Schemes Part 3 and Part 4, shown below.

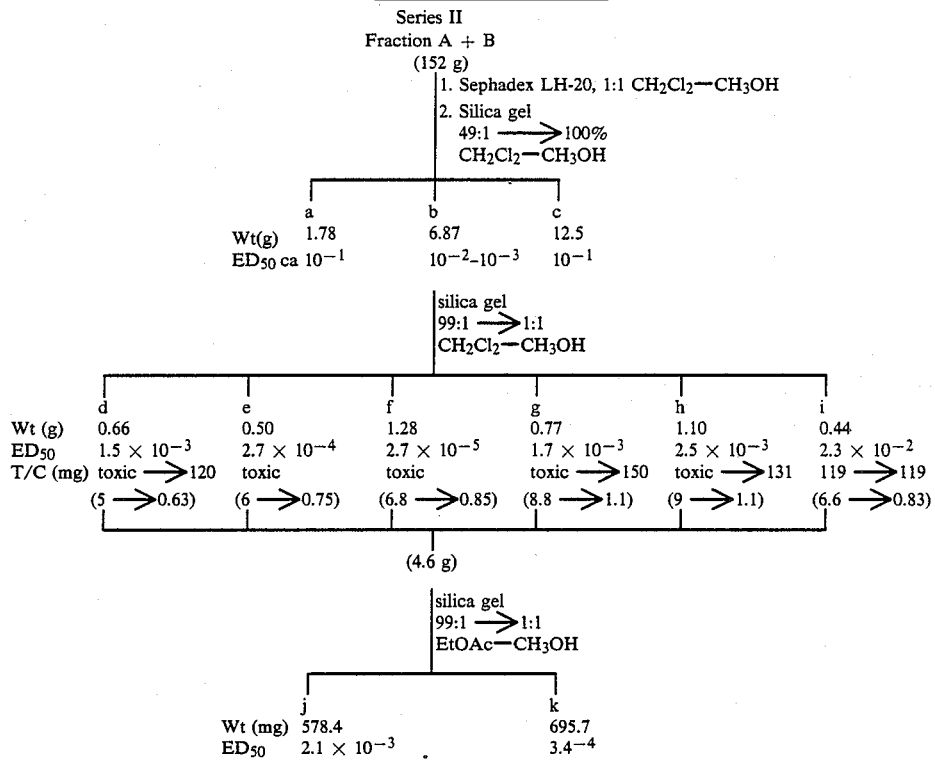

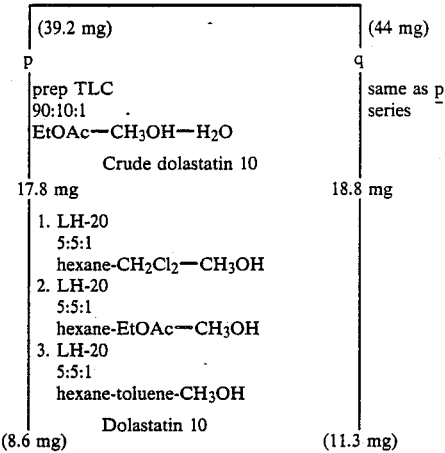

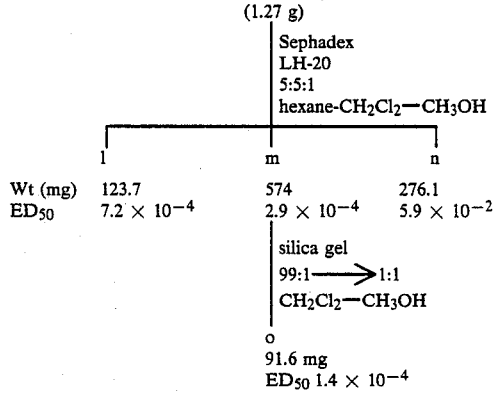

In a typical series of experiments, the 38 g of fraction A+B was chromatographed on a column of Sephadex LH-20 (10×120 cm) in 1:1 methylene chloride-methanol. Combination of similar fractions gave fractions C-J as outlined in Separation Scheme Part 1, supra. The active (in vivo) fractions D and E were combined and divided into two equal parts (6.0 each) for separation using silica gel column chromatography. The I-1 series was further separated by dry column chromatography with a gradient of 990:10:0.1 to 100:100:1 ethyl acetate-methanol-water to give active fractions K, L, and M. The parallel I-2 series was also separated by dry column chromatography using methylene chloride-methanol and the gradient 99:1 to 1:1 giving active fraction N. Combined fractions K, L, M (2.6 g) were separated using dry column silica gel chromatography and a 99:1 to 1:1 methylene chloride-methanol gradient to give active fractions O-S (1.15 g) as detailed on Separation Scheme Part 2, supra. The combined active fractions O-S were then separated again on a column of silica gel, using a 99:1 to 4:1 methylene chloride-methanol gradient that resulted in 155.8 mg of active material. The latter fraction was further separated on a column of silica gel (wet) using 99:1 to 1:1 ethyl acetate-methanol to give active fractions V and W. Combined V and W (7.4 mg) was finally separated by three steps including preparative TLC with 9:1:0.8 methylene chloride-methanol-water and again with 9:1:0.1 ethyl acetate-methanol-water followed by partition chromatography using Sephadex LH-20 and 5:5:1 hexane-methylene chloride as solvent. Thus, series I-1 led to 5.0 mg of dolastatin 10. Continuation of the separation with Series I-2 yielding fraction N (0.58 g) required an LH-20 Sephadex partition separation with the 4:5:1 hexane-methylene chloride-methanol solvent system. Active fractions T and U were combined (0.19 g) and further purified on columns of silica gel (wet with solvent) employing a 99:1 to 1:1 methylene chloride-methanol gradient. The resulting active fraction (18.1 mg) was finally purified using HPLC (ODS-2 column) with a 1:1 to 9:1 methanol-water gradient. Series I-2 yielded 3.8 mg of pure dolastatin 10.

The larger amount of fraction A+B (152 g) was chromatographed on columns (10×120 cm) of Sephadex LH-20 in five portions in 1:1 methylene chloride-methanol as described in Series II, Separation Scheme Part 3, supra. The active fractions were combined and further separated using a column (4.5×80 cm; 1.2 kg) of silica gel and a stepwise gradient of methylene chloride-methanol (49:1 23:2, 9:1, 22:3, 17:3, 4:1, 1:1 and lastly, 100% methanol) to give active fraction b (6.87 g). Fraction b was rechromatographed on silica gel (dry) using a 99:1 to 1:1 methylene chloride-methanol gradient. The resulting active fractions d-i (4.6 g) were combined and chromatographed (dry column) on silica gel using a 99:1 to 1:1 ethyl acetate-methanol gradient to give active fractions j and k (1.27 g). Both fractions (j and k combined) were chromatographed on Sephadex LH-20 using a 5:5:1 hexane-methylene chloride-methanol partition system to afford active fraction m. Separation of fraction m on silica gal (Size B Merck prepack) with a 99:1 to 1:1 methylene chloride-methanol gradient procedure gave active fractions p (39.2 mg) and q (44 mg) as outlined in Separation Scheme Series II Part 4, infra. At this point, fractions p and q were purified separately in parallel using preparative TLC (90:10:1 ethyl acetate-methanol-water mobile phase) followed by successive Sephadex LH-20 partition steps with 5:5:1 hexane-methylene chloride-methanol. 5:5:1 hexane-ethyl acetate-methanol and lastly the 5:5:1 hexane-toluene-methanol solvent system. Fraction p gave 8.6 mg and fraction q 11.3 mg of pure dolastatin 10: total yield, 28.7 mg of amorphous (colorless) powder (mp 107°–112°) from methylene chloride-methanol; TLC (Table III, visualization found best by UV light or iodine vapor); $[\alpha]_D^{29} -68.0$ (c, 0.01, $CH_3OH$); UV ($CH_3OH$) λmax 209 (ε 8,100), 216 (ε 20,180) and 242 (ε 3,609) nm,; IR (KBr) γmax 2975, 2940, 2890, 2870, 1680, 1650, 1540, 1460, 1390, 1100, 750, and 700 cm-$^1$H- and C-NMR (see Table II); and HREIMS (Tables I and III) m/z 784.4890 (calcd for $C_{42}H_{68}N_6O_6S$, 784.4922); ESCA for sulfur (one). The thin layer chromatographic properties of Dolastatin 10 are shown in Table III.

The suprisingly remarkable anticancer activity of Dolastatin 10 has been summarized in Table IV.

TABLE III

Thin Layer Chromatographic Properties of Dolastatin 10

| Substrate | Solvent System | | $R_f$ Value |
|---|---|---|---|
| Silica gel | $CH_2Cl$—$CH_3OH$—$H_2O$ | 90:10:0.8 | 0.38 |
| Silica gel | $CH_2Cl_2$—$CH_3OH$—$H_2O$—$NH_4OH$ | 90:10:0.8:0.2 | 0.43 |
| Silica gel | EtOAc—$CH_3OH$—$H_2O$ | 90:10:1.0 | 0.31 |
| Silica gel | EtOAc—$CH_3OH$—$H_2O$—$NH_4OH$ | 90:10:1.0:0.2 | 0.37 |
| RP-8 | $CH_3CN$—$H_2O$ | 3:1 | 0.42 |
| RP-8 | $CH_3OH$—$H_2O$ | 3:1 | 0.19 |
| RP-18 | $CH_3CN$—$H_2O$ | 3:1 | 0.27 |
| RP-18 | $CH_3OH$—$H_2O$ | 3:1 | 0.12 |

TABLE IV

Anticancer Activity of Dolastatin 10 (NSC 376128), Murine In Vivo System, T/C (μg/kg)

| P388 Lymphocytic Leukemia | L1210 Lymphocytic Leukemia |
|---|---|
| toxic (08–27) | toxic (26) |
| 173 (13.5) | 152 (13) |
| 161 (8) | 135 (6.5) |
| 202 (4) | 139 (3.25) |
| 199 (2) | 120 (1.63) |
| B16 Melanoma | M5076 Ovary Sarcoma |
| 238 (11.11) | toxic (24) |
| 182 (6.67) | toxic (26) |
| 205 (4.0) | 166 (13) |
| 171 (3.4) | 142 (6.5) |
| 142 (1.44) | 151 (3.25) |
| Human Melanoma Xenograph to Nude Mouse (LOX) | Human Mammary Xenograph to nude Mouse MX-1 (life extension) |
| toxic and 66.6% cures (52) | toxic (52) |
| 301 and 50% cures (26) | toxic (26) |
| 301 and 33.3% cures (13) | 137 (13) |
| 206 and 16.6% cures (6.5) | 178 (6.25) |
| 170 (3.25) | |

| MX-1 Tumor Regression |
|---|
| 14 (52) |
| 50 (26) |
| 61 (13) |
| 69 (6.25) |

T/C = Test/Control, both bearing tumor, expressed in time of survival.
T/C − 100 = % life extension Hyrdrolysis of Dolastatin 10

Small samples of dolastatin 10 were subjected to various hydrolysis conditions as summarized in Table IV. The presence of valine and phenylalanine was ascertained by these procedures.

Attempted Saponification and Acetylation of Dolastatin 10

A sample (0.1 mg) of dolastatin 10 was treated with a solution prepared from 0.1 mL of 0.1N sodium hydroxide and 0.1 mL of methanol at room temperature for 6 h. The resulting solution was acidified and solvent removed (nitrogen stream). Analysis of the residue by TLC showed a single component with an Rf identical to dolastatin 10.

A 0.1 mg amount of dolastatin 10 was treated with acetic anhydride (0.07 mL)-pyridine (0.1 mL) at room temperature for 24 h. The solvent was evaporated under nitrogen and the residue was analyzed by TLC. A single component was observed and its Rf was identical to that of dolastatin 10.

The administration of dolastatin 10, its synthetic counterpart, and its parmacologically active physiologically compatible derivatives is useful for treating animals or humans bearing a neoplastic disease, for example, acute myelocytic leukemia, acute lymphocytic leukemia, malignant melanoma, adenocarcinoma of lung, neuroblastoma, small cell carcinoma of lung, breast carcinoma, colon carcinoma, ovarian carcinoma, bladder carcinoma, and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 20 mg/kg; intramuscular, 1 to about 50 mg/kg; orally, 5 to about 100 mg/kg; intranasal instillation, 5 to about 100 mg/kg; and aerosol, 5 to about 100 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as a talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, decalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and a polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably pyrogen free ("P.F.") water. A dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof.

EXAMPLE 1

Several dosage forms were prepared embodying the present invention. They are shown in the following examples in which the notation "active ingredient" signifies dolastatin 10, its synthetic counterpart and the non-toxic pharmaceutically active derivatives thereof.

COMPOSITION "A"

Hard-Gelatin Capsules

One thousand two-piece hard gelatin capsules for oral use, each capsule containing 20 mg of an active ingredient are prepared from the following types and amounts of ingredients:

| Active ingredient, micronized | 20 gm |
|---|---|
| Corn Starch | 20 gm |
| Talc | 20 gm |
| Magnesium stearate | 2 gm |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing a active ingredient in 5, 25 and 50 mg amounts by substituting 5 gm, 25 gm and 50 gm of an active ingredient for the 20 gm used above.

COMPOSITION "B"

Soft Gelatin Capsules

One-piece soft gelatin capsules for oral use, each containing 20 mg of an active ingredient (finely divided by means of an air micronizer), are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 20 mg of an active ingredient are prepared from the following types and amounts of ingredients:

| Active ingredient micronized | 20 gm |
|---|---|
| Lactose | 300 gm |
| Corn starch | 50 gm |
| Magnesium stearate | 4 gm |
| Light liquid petrolatum | 5 gma |

The active ingredient finely divided by means of an air micronizer, is added to the other ingredients and then thoroughly mixed and slugged. The slugs are broken down by forcing through a Number Sixteen screen. The resulting granules are then compressed into tablets, each tablet containing 20 mg of the active ingredient.

The foregoing tablets are useful for treating a neoplastic disease by the oral administration of one or two tablets one to four times a day.

Using the procedure above, tablets are similarly prepared containing an active ingredient in 25 mg and 10 mg amounts by substituting 25 gm and 10 gm of an active ingredient for the 20 gm used above.

COMPOSITION "D"

Oral Suspension

One thousand ml of an aqueous suspension for oral use, containing in each teaspoonful (5 ml) dose, 5 mg of an active ingredient, is prepared from the following types and amounts of ingredients:

| Active ingredient micronized | 1 gm |
|---|---|
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml. | |

The citric acid, benzoic acid, sucrose, tragacanth and lemon oil are dispersed in sufficient water to make 850 ml of suspension. The active ingredient finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION "E"

Parenteral Product

A sterile aqueous suspension for parenteral injection, containing in 1 ml, 30 mg of an active ingredient for treating a neoplastic disease, is prepared from the following types and amounts of ingredients:

| Active ingredient, micronized | 30 gm |
|---|---|
| Polysorbate 80 | 5 gm |
| Methylparaben | 2.5 gm |
| Propylparaben | 0.17 gm |
| Water for injection, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 M) three times a day.

COMPOSITION "F"

Suppository, Rectal and Vaginal

One thousand suppositories, each weighing 2.5 gm and containing 20 mg of an active ingredient are prepared from the following types and amounts of ingredients:

| | |
|---|---|
| Active ingredient, micronized | 1.5 gm |
| Propylene glycol | 150 gm |
| Polyethylene glycol #4000, q.s. | 2,500 gm |

The active ingredient is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository is foil wrapped.

The foregoing suppositories are inserted rectally or vaginally for treating a neoplastic disease.

COMPOSITION "G"

Intranasal Suspension

One thousand ml of a sterile aqueous suspension for intranasal instillation, containing in each ml 20 mg of an active ingredient, is prepared from the following types and amounts of ingredients:

| | |
|---|---|
| Active ingredient, micronized | 1.5 gm |
| Polysorbate 80 | 5 gm |
| Methylparaben | 2.5 gm |
| Propylparaben | 0.17 gm |
| Deionized water, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

Ten grams of an active ingredient in bulk form is finely divided by means of an air micronizer. The micronized powder is divided into individual doses of 20 mg and packaged.

The foregoing powders are useful for treating a neoplastic disease, by the oral administration of one or two powders suspended in a glass of water, one to four times per day.

COMPOSITION "J"

Insufflation

Ten grams of an active ingredient in bulk form is finely divided by means of an air micronizer.

The foregoing composition is useful for treating a neoplastic disease, by the inhalation of 30 mg one to four times per day.

COMPOSITION "K"

Hard Gelatin Capsules

One hundred two-piece hard gelatin capsules for oral use, each capsule containing 20 mg of an active ingredient.

The active ingredient is finely divided by means of an air micronizer and encapsulated in the usual manner.

The foregoing capsules are useful for treating a neoplastic disease, by the oral administration of one or two capsules, one to four times a day.

Using the procedure above, capsules are similarly prepared containing active ingredient in 5, 25 and 50 mg amounts by substituting 5 gm, 25 gm and 50 gm of the active ingredient for the 20 gm used above.

EXAMPLE 2

Unit dosage forms of dolastatin 10 prepared according to selected compositions described in Example 1 were screened utilizing Protocol 1,200 described in *Cancer Chemotherapy Reports*, parts 3, Vol. 3, No. 2, September 1972, pp 9 et seq for lymphocytic leukemia P388. Dolastatin 10 provided a 69–102% life extension at 1–4 µg/Kg host body weight against the murine P388 lymphocytic leukemia. Dolastatin 10 also markedly inhibited growth of the P388 in vitro cell line ($ED_{50} = 4.6 \times 10^{-5}$ µg/ml).

EXAMPLE 3

Unit dosage forms of dolastatin 10 were prepared according to Example 1 and were screened using accepted protocols of the National Cancer Institute. The preparation obtained a 17–67% cure rate at 3.25–26 µg/kg host body weight against NCI murine human melanoma xenograph.

EXAMPLE 4

A unit dosage form of dolastatin 10, prepared according to Example 1, was challenged with B-16 murine melanoma and obtained a 42% to 138% life extension at 1.44 to 11.1 µg/Kg using the National Cancer Institute accepted protocol.

From the foregoing it becomes readily apparent that a new and useful antineoplastic factor and new and useful antineoplastic preparations have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention which is limited only by the scope of the claims appended hereto.

Accordingly, what is claimed is:

1. A cell growth inhibitory substance denominated dolastatin 10 and having the structural formula:

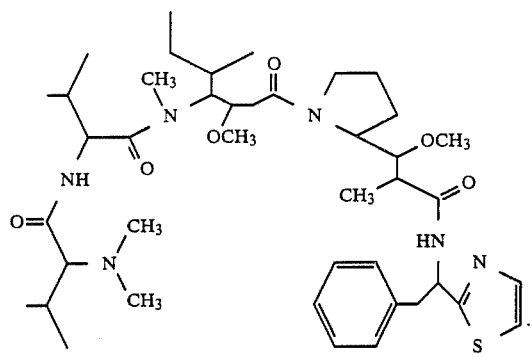

2. A pharmaceutical preparation comprising a pharmaceutically acceptable carrier and an effective amount of a natural or synthetic cell growth inhibitory substance or a non-toxic pharmaceutical active derivative thereof, said substance having the structural formula:

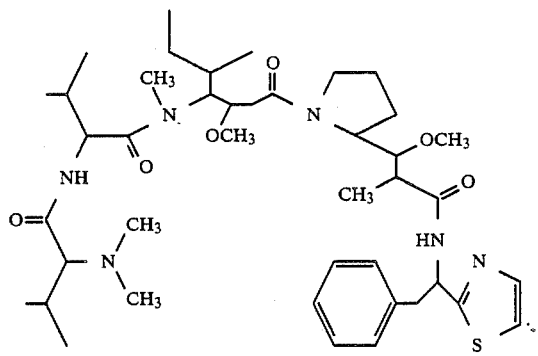

3. A cell growth inhibitory substance according to claim 1 having the following N.M.R. characteristics:

| Structure Assignment | 13C(mult) | $^1$H(mult; J,Hz; Integration) | NOE |
|---|---|---|---|
| 2 | 170.51(s) | 7.717(d; 3.3; 1H) | |
| 4 | 142.77(d) | 7.254(d; 3.3; 1H) | |
| 5 | 118.76(d) | 5.516(ddd; 5.7,7.2, 9.3; 1H) | |
| 6 | 53.02(d) | 3.399(dd; 5.7,14; 1H) | |
| 6a | 41.48(t) | 3.256(dd; 5.7; 14; 1H) | |
| 6b1 | 137.74(s) | 7.243(d; 7.9; 2H) | |
| 6b2,6b6 | 128.74(d)×2 | 7.214(dd; 7.9,9.2; 2H) | |
| 6b3,6b5 | 129.80(d)×2 | 7.194(t; 9.2; 1H) | |
| 6b4 | 127.02(d) | 7.256(t; 7.6; 1H) | |
| 7 | | | 9,9a,10, 10ab,11 |
| 8 | 175.67(s) | 2.282(quintet; 7.2; 1H) | 7 |
| 9 | 44.79(d) | 1.085(d; 7.1; 3H) | |
| 9a | 14.49(q) | 3.845(dd; 2.0,8.2; 1H) | 7 |
| 10 | 82.05(d) | 3.309(s; 3H) | 6,7 |
| 10ab | 60.89(q) | 3.985(m; 1H) | |
| 11 | 59.86(d) | 1.804(ddd; 5.5,7.0; 19; 1H) | |
| 12 | 25.00(t) | 1.608(ddd; 7; 9.2,19; 1H) 1.446(ddd; 4.7,7,19; 1H) | |
| 13 | 25.45(t) | 1.715(ddd; 4.7,7.8,12.7; 1H) 3.401(dd; 7.8,10; 1H) | 17 |
| 14 | 48.03(t) | 3.390(m; 1H)$^b$ | |
| 16 | 174.01(s) | | |
| 17 | 38.11(t) | 2.394(ABq; 9.0; 2H) | 14 |
| 18 | 78.86(d) | 4.122(broad t; 8.7; 1H) | |
| 18ab | 58.16(q) | 3.313(s; 3H) | 22 |
| 19 | 54.11(d) | 3.26–3.39(1H)$^c$ | |
| 19a | 33.62(d) | 1.680(1H)$^b$ | |
| 19b | 26.25(t) | 1.370(broad m; 1H) 1.000(broad m; 1H)$^b$ | |
| 19c | 10.92(q) | 0.823(t; 7.4; 3H) | |
| 19d | 19.82(q) | 1.003(d; 6.8; 3H) | |
| 20a | 30.09(q) | 3.012(s; 3H) | 22 |
| 21 | 171.39(s) | | |
| 22 | 54.20(d) | 4.761(dd; 6.5, 8.8; 1H) | 18,18ab, 20,19 |
| 22a | 31.42(d) | 1.983(sextet; 6.7; 1H) | |
| 22b | 18.18(q) | 0.941(d; 6.8; 3H) | |
| 22c | 16.09(q) | 0.977(d; 6.8; 3H) | |
| 23 | | 6.861(d; 8.9; 1H) | 25bc |
| 24 | 172.44(s) | | |
| 25 | 76.77(d) | 2.454(d; 6.9; 1H) | 23 |
| 25bc | 49.92(q)×2 | 2.262(s; 6H) | 23 |
| 26 | 28.08(d) | 2.073(sextet; 6.7; 1H) | |
| 27 | 20.24(q) | 0.964(d; 6.8; 3H) | |
| 28 | 18.18(q) | 0.902(d; 6.8; 3H) | |

$^a$Residual CHDCl$_2$ as internal reference (5.32 ppm).
$^b$Overlapping signal.
$^c$Signal assigned from NOE data.

4. A pharmaceutical preparation according to claim 2 in which said substance has the following N.M.R. characteristics:

| Structure Assignment | 13C(mult) | $^1$H(mult; J,Hz; Integration) | NOE |
|---|---|---|---|
| 2 | 170.51(s) | 7.717(d; 3.3; 1H) | |
| 4 | 142.77(d) | 7.254(d; 3.3; 1H) | |
| 5 | 118.76(d) | 5.516(ddd; 5.7,7.2, 9.3; 1H) | |
| 6 | 53.02(d) | 3.399(dd; 5.7,14; 1H) | |
| 6a | 41.48(t) | 3.256(dd; 5.7; 14; 1H) | |
| 6b1 | 137.74(s) | 7.243(d; 7.9; 2H) | |
| 6b2,6b6 | 128.74(d)×2 | 7.214(dd; 7.9,9.2; 2H) | |
| 6b3,6b5 | 129.80(d)×2 | 7.194(t; 9.2; 1H) | |
| 6b4 | 127.02(d) | 7.256(t; 7.6; 1H) | |
| 7 | | | 9,9a,10, 10ab,11 |
| 8 | 175.67(s) | 2.282(quintet; 7.2; 1H) | 7 |
| 9 | 44.79(d) | 1.085(d; 7.1; 3H) | |
| 9a | 14.49(q) | 3.845(dd; 2.0,8.2; 1H) | 7 |
| 10 | 82.05(d) | 3.309(s; 3H) | 6,7 |
| 10ab | 60.89(q) | 3.985(m; 1H) | |
| 11 | 59.86(d) | 1.804(ddd; 5.5,7.0; 19; 1H) | |
| 12 | 25.00(t) | 1.608(ddd; 7; 9.2,19; 1H) 1.446(ddd; 4.7,7,19; 1H) | |
| 13 | 25.45(t) | 1.715(ddd; 4.7,7.8,12.7; 1H) 3.401(dd; 7.8,10; 1H) | 17 |
| 14 | 48.03(t) | 3.390(m; 1H)$^b$ | |
| 16 | 174.01(s) | | |
| 17 | 38.11(t) | 2.394(ABq; 9.0; 2H) | 14 |
| 18 | 78.86(d) | 4.122(broad t; 8.7; 1H) | |
| 18ab | 58.16(q) | 3.313(s; 3H) | 22 |
| 19 | 54.11(d) | 3.26–3.39(1H)$^c$ | |
| 19a | 33.62(d) | 1.680(1H)$^b$ | |
| 19b | 26.25(t) | 1.370(broad m; 1H) 1.000(broad m; 1H)$^b$ | |
| 19c | 10.92(q) | 0.823(t; 7.4; 3H) | |
| 19d | 19.82(q) | 1.003(d; 6.8; 3H) | |
| 20a | 30.09(q) | 3.012(s; 3H) | 22 |
| 21 | 171.39(s) | | |
| 22 | 54.20(d) | 4.761(dd; 6.5, 8.8; 1H) | 18,18ab, 20,19 |
| 22a | 31.42(d) | 1.983(sextet; 6.7; 1H) | |
| 22b | 18.18(q) | 0.941(d; 6.8; 3H) | |
| 22c | 16.09(q) | 0.977(d; 6.8; 3H) | |
| 23 | | 6.861(d; 8.9; 1H) | 25bc |
| 24 | 172.44(s) | | |
| 25 | 76.77(d) | 2.454(d; 6.9; 1H) | 23 |
| 25bc | 49.92(q)×2 | 2.262(s; 6H) | 23 |
| 26 | 28.08(d) | 2.073(sextet; 6.7; 1H) | |

-continued

| Structure Assignment | Chemical Shift, ppm | | NOE |
|---|---|---|---|
| | 13C(mult) | 1H(mult; J,Hz; Integration) | |
| 27 | 20.24(q) | 0.964(d; 6.8; 3H) | |
| 28 | 18.18(q) | 0.902(d; 6.8; 3H) | |

[a]Residual CHDCl₂ as internal reference (5.32 ppm).
[b]Overlapping signal.
[c]Signal assigned from NOE data.

5. A method of treating a host afflicted with neoplastic disease comprising administering to said host an effective amount of a natural or synthetic cell growth inhibitory substance or a pharmaceutically active non-toxic derivative thereof, said substance having the structural formula:

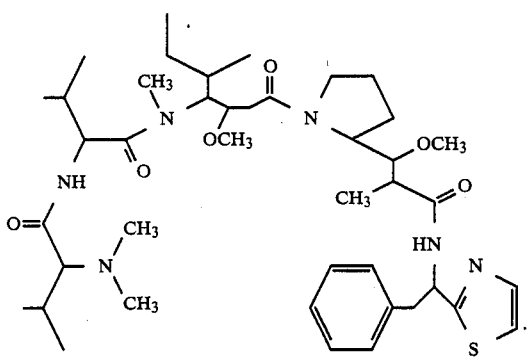

6. A method according to claim 5 in which said substance is administered intravenously, at a dosage level of from 0.1 up to about 20 mg per kilogram of host body weight.

7. A method according to claim 5 in which said substance is administered subcutaneously, at a dosage level of from 1 up to about 50 mg per kilogram of host body weight.

8. A method according to claim 5 in which said substance is administered orally, at a dosage level of from 5 up to about 100 mg per kilogram of host body weight.

9. A method according to claim 5 in which said neoplastic disease is lymphocytic leukemia P388.

10. A method according to claim 9 in which said small but effective amount comprises from about 1 up to about 4 µg per kilogram of host body weight.

11. A method according to claim 5 in which said substance has the following N.M.R. characteristics:

| Structure Assignment | Chemical Shift, ppm | | NOE |
|---|---|---|---|
| | 13C(mult) | 1H(mult; J,Hz; Integration) | |
| 2 | 170.51(s) | 7.717(d; 3.3; 1H) | |
| 4 | 142.77(d) | 7.254(d; 3.3; 1H) | |
| 5 | 118.76(d) | 5.516(ddd; 5.7,7.2, 9.3; 1H) | |
| 6 | 53.02(d) | 3.399(dd; 5.7,14; 1H) | |
| 6a | 41.48(t) | 3.256(dd; 5.7; 14; 1H) | |

-continued

| Structure Assignment | Chemical Shift, ppm | | NOE |
|---|---|---|---|
| | 13C(mult) | 1H(mult; J,Hz; Integration) | |
| 6b1 | 137.74(s) | 7.243(d; 7.9; 2H) | |
| 6b2,6b6 | 128.74(d)×2 | 7.214(dd; 7.9,9.2; 2H) | |
| 6b3,6b5 | 129.80(d)×2 | 7.194(t; 9.2; 1H) | |
| 6b4 | 127.02(d) | 7.256(t; 7.6; 1H) | |
| 7 | | | 9,9a,10, 10ab,11 |
| 8 | 175.67(s) | 2.282(quintet; 7.2; 1H) | 7 |
| 9 | 44.79(d) | 1.085(d; 7.1; 3H) | |
| 9a | 14.49(q) | 3.845(dd; 2.0,8.2; 1H) | 7 |
| 10 | 82.05(d) | 3.309(s; 3H) | 6,7 |
| 10ab | 60.89(q) | 3.985(m; 1H) | |
| 11 | 59.86(d) | 1.804(ddd; 5.5,7.0; 19; 1H) | |
| 12 | 25.00(t) | 1.608(ddd; 7; 9.2,19; 1H) 1.446(ddd; 4.7,7,19; 1H) | |
| 13 | 25.45(t) | 1.715(ddd; 4.7,7.8,12.7; 1H) 3.401(dd; 7.8,10; 1H) | 17 |
| 14 | 48.03(t) | 3.390(m; 1H)[b] | |
| 16 | 174.01(s) | | |
| 17 | 38.11(t) | 2.394(ABq; 9.0; 2H) | 14 |
| 18 | 78.86(d) | 4.122(broad t; 8.7; 1H) | |
| 18ab | 58.16(q) | 3.313(s; 3H) | 22 |
| 19 | 54.11(d) | 3.26–3.39(1H)[c] | |
| 19a | 33.62(d) | 1.680(1H)[b] | |
| 19b | 26.25(t) | 1.370(broad m; 1H) 1.000(broad m; 1H)[b] | |
| 19c | 10.92(q) | 0.823(t; 7.4; 3H) | |
| 19d | 19.82(q) | 1.003(d; 6.8; 3H) | |
| 20a | 30.09(q) | 3.012(s; 3H) | 22 |
| 21 | 171.39(s) | | |
| 22 | 54.20(d) | 4.761(dd; 6.5, 8.8; 1H) | 18,18ab, 20,19 |
| 22a | 31.42(d) | 1.983(sextet; 6.7; 1H) | |
| 22b | 18.18(q) | 0.941(d; 6.8; 3H) | |
| 22c | 16.09(q) | 0.977(d; 6.8; 3H) | |
| 23 | | 6.861(d; 8.9; 1H) | 25bc |
| 24 | 172.44(s) | | |
| 25 | 76.77(d) | 2.454(d; 6.9; 1H) | 23 |
| 25bc | 49.92(q)×2 | 2.262(s; 6H) | 23 |
| 26 | 28.08(d) | 2.073(sextet; 6.7; 1H) | |
| 27 | 20.24(q) | 0.964(d; 6.8; 3H) | |
| 28 | 18.18(q) | 0.902(d; 6.8; 3H) | |

[a]Residual CHDCl₂ as internal reference (5.32 ppm).
[b]Overlapping signal.
[c]Signal assigned from NOE data.

12. A method according to claim 5 in which said neoplastic disease is murine melanoma.

13. A method according to claim 12 in which said small but effective amount comprises from about 1.44 up to about 11.1 µg per kilogram of host body weight.

14. A method according to claim 5 in which said neoplastic disease is human melanoma.

15. A method according to claim 14 in which said small but effective amount comprises from about 3.25 up to about 26 µg per kilogram of host body weight.

16. A method according to claim 11 in which said substance is administered intravenously, at a dosage level of from 0.1 up to about 20 mg per kilogram of host body weight.

17. A method according to claim 11 in which said substance is administered subcutaneously, at a dosage level of from 1 up to about 50 mg per kilogram of host body weight.

18. A method according to claim 11 in which said substance is administered orally, at a dosage level of from 5 up to about 100 mg per kilogram of host body weight.

* * * * *